United States Patent [19]

Kreider et al.

[11] Patent Number: 5,071,757
[45] Date of Patent: Dec. 10, 1991

[54] METHODS FOR PROPAGATING FASTIDIOUS HUMAN VIRUSES AND FOR PRODUCING PURIFIED SUSPENSIONS THEREOF

[76] Inventors: John W. Kreider, Box 297, R.D. 1, Palmyra, Pa. 17078; Mary K. Howett, 2309 Bellevue Rd., Harrisburg, Pa. 17104

[21] Appl. No.: 294,744

[22] Filed: Jan. 9, 1989

Related U.S. Application Data

[62] Division of Ser. No. 915,577, Oct. 6, 1986, Pat. No. 4,814,268.

[51] Int. Cl.$^5$ .......................... C12N 7/02; C12N 7/00; C12N 1/00; A61K 39/12
[52] U.S. Cl. .................................. 435/239; 435/235.1; 435/236; 435/237; 435/238; 435/948; 424/89
[58] Field of Search ............... 435/239, 235, 236, 237, 435/238, 948; 424/89

[56] References Cited

U.S. PATENT DOCUMENTS 4,689,225  8/1987  Pereira .

OTHER PUBLICATIONS

European Patent Office Publication 174-228-A, published Mar. 12, 1986.
Caunt and Taylor-Robinson, T. Hyg. Camb., 62:413-424 (1964).
"Assay of Viruses," in Essentials of Medical Microbiology (Volk et al. Eds.), Third Edition (1986), pp. 600-602.
Kreider et al., Nature, 317:639-641 (1985).
Olsen et al., Regulatory Peptides, 10:37-45 (1984).
Kreider et al., Cancer Research, 39:273-276 (1979).
Watts et al., Science, 225:634-636 (1984).
Yassumoto et al., J. Virology, 57:572-577 (1986).
Kreider et al., J. Investigative Dermatology, 57:66-71 (1971).
Pass et al., J. Investigative Dermatology, 61:371-374 (1973).
Cubie, British Journal of Dermatology, 94:659-665 (1976).
Joklik, et al., Zinsser Microbiology, 17th Ed. (Appleton--Century Crofts, New York, 1980), pp. 1002-1008, 1034-1036.
Cukor and Blacklow, "Human Viral Gastroenteritis," Microbiological Review, 48:157-179 (1984).
Barnett, "Viral Gastroenteritis," Medical Clinics of North America, 67:1031-1058 (1983).
Murphy, "Aetiology of Viral Gastroenteritis: A Review," Med. J. Aust., 2:177-182 (1981).

Primary Examiner—Robert A. Wax
Assistant Examiner—Bradley L. Sisson
Attorney, Agent, or Firm—Dickstein, Shapiro & Morin

[57] ABSTRACT

Processes for propagating a fastidious human virus in the laboratory and producing purified viral suspensions of such a virus are disclosed. The virus is extracted from tissue which contains it, and the extract is used to infect human tissue known to be susceptible to that virus. The infected tissue is placed beneath the renal capsule of an immuno-compromised animal and allowed to remain in the animal until recoverable quantities of the virus are produced. The virus is then recovered from the infected tissue and is purified. Also disclosed are variations of the process, used for detecting a fastidious human virus, for determining the infectivity of a sample containing a fastidious human virus, or for determining the antiviral activity of a substance. Finally, purified suspensions of fastidious human viruses and compositions useful as vaccines are disclosed.

19 Claims, No Drawings

METHODS FOR PROPAGATING FASTIDIOUS HUMAN VIRUSES AND FOR PRODUCING PURIFIED SUSPENSIONS THEREOF

U.S. GOVERNMENT RIGHTS

The invention described herein was made in the course of work under a grant or award from the National Institutes of Health. The U.S. Government has certain rights in this invention pursuant to such grant or award.

This application is a division of application Ser. No. 915,577, filed Oct. 6, 1986, now U.S. Pat. No. 4,814,268.

BACKGROUND OF THE INVENTION

This invention relates to methods for propagating fastidious human viruses in the laboratory, and producing purified viral suspensions of such viruses. It also relates to methods of determining the infectivity of samples containing these viruses and assays for determining the antiviral activity of substances.

The scientific study of many disease-causing human viruses is severely hampered by the inability to grow or propagate them in vitro or in laboratory animals at all or in sufficient numbers to subject them to analytical techniques. Thus, little is known about their characteristics and the means by which they cause disease. In addition, the inability to obtain a sufficient amount of infectious virus particles at a sufficient degree of purity prevents the development of assays for the detection of the presence of the virus in samples from patients. This inability also prevents the development of vaccines or drugs to prevent or treat the diseases caused by these viruses. Thus, in many respects, the ability to make significant medical progress against a number of virus-caused illnesses in humans will depend upon the development of techniques for propagating these viruses in the laboratory.

Because of the inability or difficulty in propagating these viruses in the laboratory, they are known as fastidious viruses. Examples of such fastidious viruses include varicella-zoster virus (VZV), cytomegalovirus, various gastroenteritis viruses, and the human papillomaviruses.

VZV produces varicella (or chicken pox) and zoster. Chicken pox is a common and generally mild childhood disease. However, in adults and in immunosuppressed individuals, it can cause serious and even fatal illness. Zoster is a disease often found in adults and involves lesions similar to chicken pox. It is the manifestation of the reactivation of an earlier varicella infection. It can lead to a number of complications and can be particularly serious for immunosuppressed patients. See Joklik et al., *Zinsser Microbiology*, 17th Ed. (Appleton-Century Crofts, New York, 1980), pp. 1002-1005.

Humans are apparently the only natural host for VZV. Although VZV has been grown in tissue culture, it remains cell associated and is rapidly inactivated when the host cell is disrupted.

Cytomegalovirus, which is related to VZV in that both are members of the herpesvirus family, is responsible for a broad spectrum of disease affecting humans in many different clinical settings. It is the most common cause of congenital viral infection, it is an etiologic agent of mononucleosis, and is a life-threatening pathogen in immuno-compromised patients. See Joklik et al., *Zinsser Microbiology*, 17th Ed. (Appleton-Century Crofts, New York, 1980), pp. 1005-1008.

A number of viruses are implicated in acute gastroenteritis, a problem encountered daily by physicians. In developed countries, acute gastroenteritis is second only to the common cold in frequency of occurrence. The illness can be serious and even life-threatening in the elderly, the young, and the debilitated patient. The two most frequently implicated viruses are rotaviruses and the Norwalk virus (and Norwalk-like viruses).

These and other suspected agents of human viral gastroenteritis have been very fastidious with respect to cultivation by in vitro techniques or in laboratory animal hosts. Thus, the studies of these agents have been hampered, and current methods of detecting their presence leave much to be desired. Similarly, vaccine development and methods of prevention and treatment have been extremely hampered. The cultivation of these viral agents will facilitate the development of diagnostic reagents and the development and evaluation of vaccines. See Cukor and Blacklow, "Human Viral Gastroenteritis," *Microbiological Reviews*, 48: 157-179 (1984); Barnett, "Viral Gastroenteritis," *Medical Clinics of North America*, 67: 1031-1058 (1983); and Murphy, Aetiology of Viral Gastroenteritis: "A Review," *Med. J. Aust.*, 2: 177-182 (1981).

The human papillomaviruses are a heterogeneous group of viruses that induce epithelial or fibroepithelial proliferations of skin or mucosa. Over 40 types of human papillomavirus (HPV) are recognized, many of which are associated with distinctive lesions. Specific diseases associated with HPV infection, such as common warts, epidermodysplasia verruciformis, and genital warts (condylomas), correlate with specific HPV types. For example, HPV-1 has been shown to produce skin warts, and HPV-11 has been shown to produce genital warts. The latter type can also produce warts on the vocal cords of newborns who have been infected by their mothers. Such warts are a serious problem to the newborns because they threaten breathing and must be surgically removed.

Recent studies have implicated HPVs in the development of premalignant and malignant lesions of the skin (Ikenberg et al., *Int. J. Cancer*, 32: 563-565, 1983; Orth et al., *Cancer Res.*, 39: 1074-1082, 1979), uterine cervix (Durst et al., *Proc. Natl. Acad. Sci.*, 80: 3812-3815, 1983), and larynx (Galloway et al., *Arch. Otol.*, 72: 289-294, 1960). For example, HPV-16 and HPV-18 has been isolated and molecularly cloned from cervical carcinoma cells and are strongly associated with cervical carcinomas. However, the biological significance of the association of HPV-16 and HPV-18 DNA with cervical cancer has not yet been determined.

Studies on the contribution of HPVs to the etiology of human tumors have been severely restricted by the unavailability of laboratory animal hosts or culture systems that would allow neoplastic transformation and/or viral replication. Many unsuccessful attempts have been made to develop tissue culture systems or find laboratory animal hosts for HPV. However, these viruses are fastidious in their growth requirements, being host and cell specific and requiring an epithelial cell in an advanced state of differentiation for replication. HPV infection of human subjects is, of course, ethically unacceptable.

With respect to attempts to grow HPV in tissue culture, recent studies report only that HPV DNA can persist in and transform cultured cells. See La Porta et al., *Proc. Natl. Acad. Sci. U.S.A.*, 79: 3393-3397, 1982, Watts et al., *Science*, 225: 634-636, 1984, and Yasumoto et al., *J. Virology*, 57: 572-577, 1986. The replication of the viruses themselves has not been reported.

Several unsuccessful attempts have been made to develop systems in which HPV-infected human tissues were grafted to immunologically privileged sites on laboratory animals or to immunologically deficient animals. Kreider et al., *J. Invest. Dermatology*, 57: 66-71, 1971 reported that human skin infected with HPV and transplanted to the cheekpouch of hamsters, which is an immunologically privileged site that accepts grafts of foreign tissues, did not produce papillomas after 14 weeks. Pass et al., *J. Invest. Dermatology*, 61: 371-374, 1973 reported that human skin grafts that had been inoculated with an extract of verrucae vulgaris and transplanted to immunosuppressed mice produced no papillomas after 14 weeks. Similarly, Cubie, *British J. Dermatology*, 94: 659-665, 1976 reported that human skin infected by HPV and grafted onto nude mice showed no papillomas after 9 weeks.

The inventors undertook to develop a method of propagating fastidious human viruses in a laboratory animal. Such a method would allow the production of a large, constant supply of these viruses for further study and testing of their association with human diseases. It would also allow the purification of the virus so that it might be used, for example, in diagnostic agents for the detection of the virus and in vaccines for the prevention of diseases caused by fastidious human viruses.

SUMMARY OF THE INVENTION

As demonstrated in the Description of the Preferred Embodiments below, the present invention involves, inter alia, a method of propagating fastidious human viruses in the laboratory. This method has resulted in a human papillomavirus being grown in the laboratory for the first time.

It is accordingly one object of the present invention to provide a method for propagating a fastidious human virus.

It is a further object to provide a method for producing a purified viral suspension of a fastidious human virus and to provide the suspension so produced.

Another object is to provide a method for producing a composition of matter which is a source of recoverable quantities of a fastidious human virus and to provide the composition so produced.

Still another object of the invention is to provide a composition of matter useful as a vaccine for a fastidious human virus.

Other objects of the invention are to provide a method to detect the presence of a fastidious virus in a sample, a method to determine the infectivity of a sample of a fastidious human virus, and methods of testing a substance to determine its activity against a fastidious human virus.

Additional objects and advantages of the invention will be set forth in part in the description which follows, and in part will be obvious from the description, or may be learned by practice of the invention. The objects and advantages of the invention will be attained by means of the instrumentalities and combinations particularly pointed out in the appended claims.

To achieve the objects and accordance with the purpose of the invention, as embodied and broadly described herein, the present invention provides a method for propagating a fastidious human virus by extracting the virus from tissue containing it, infecting human tissue known to be susceptible to the virus with the extracted virus, placing the infected human tissue beneath the renal capsule of an immuno-compromised animal, allowing the infected tissue to remain in the immuno-compromised animal until recoverable quantities of the virus are produced, and recovering the virus from the tissue. Preferably, the virus is a human papillomavirus and the human tissue is epithelial tissue.

The invention also provides a method for producing a purified suspension of a fastidious human virus comprising the additional step of purifying the virus recovered from the infected tissue which has been placed in the immuno-compromised animal. In a preferred embodiment, the fastidious human virus is a human papillomavirus.

The present invention also provides a purified suspension of a fastidious human virus. Preferably, that virus is a human papillomavirus.

The invention further provides a method for producing a composition of matter which is a source of recoverable quantities of a fastidious human virus, by extracting a fastidious human virus from tissue containing it, infecting human tissue known to be susceptible to the virus with the extract, placing the infected tissue beneath the renal capsule of an immuno-compromised animal and allowing it to remain until recoverable quantities of the virus are present in the infected tissue.

The invention further provides a composition of matter, which is a source of recoverable quantities of a fastidious human virus, wherein the composition comprises human tissue which has been infected with the virus and placed beneath the renal capsule of an immuno-compromised animal until recoverable quantities of the virus have been produced.

The invention also provides a composition of matter useful as a vaccine comprising an immunologically effective amount of attenuated or killed fastidious human virus in a pharmacologically acceptable carrier. Preferably, the fastidious human virus is a human papillomavirus.

In another embodiment, the invention provides a method to detect the presence of a fastidious human virus in a sample. The method comprises incubating the sample with human tissue known to be susceptible to the fastidious human virus, placing the human tissue beneath the renal capsule of an immuno-compromised animal, allowing the tissue to remain in the immuno-compromised animal for a period of time sufficient to produce an effect in the tissue substantially identical to the effect produced by the virus when the virus naturally infects a human host, and determining if the effect has been produced in the tissue.

In a further embodiment, the invention provides a method for determining the infectivity of a sample of a fastidious human virus. The method comprises preparing serial dilutions of the sample, incubating each of the serial dilutions with pieces of human tissue known to be susceptible to the virus, placing each of the pieces of human tissue beneath the renal capsule of an immuno-compromised animal, allowing each of the pieces of human tissue to remain in the immuno-compromised animal for a period of time sufficient to produce an effect in the tissue substantially identical to the effect produced by the virus when a virus naturally infects a human host, determining if the effect has been produced in each of the pieces, and determining the infectivity of the sample by determining which of the serial dilutions produced the effect in one-half of the pieces of human tissue incubated with that dilution.

In still another embodiment, the invention provides methods for testing a substance to determine its activity against a human fastidious virus. One method comprises infecting human tissue known to be susceptible to the fastidious virus with the virus, contacting the substance to be tested with the infected tissue, placing the infected tissue beneath the renal capsule of an immuno-compromised animal, allowing the tissue to remain in the animal for a period of time sufficient to produce an effect in the tissue substantially identical to the effect produced by the virus when the virus naturally infects a human host, and determining if the effect has been produced. Another method comprises infecting human tissue known to be susceptible to the fastidious human virus with the virus, placing the infected tissue beneath the renal capsule of an immuno-compromised animal, administering the substance to be tested to the animal, allowing the tissue to remain in the animal for a period of time sufficient to produce an effect in the tissue substantially identical to the effect produced by the virus when the virus naturally infects a human host, and determining if the effect has been produced.

DESCRIPTION OF THE PREFERRED EMBODIMENTS

Reference will now be made in detail to the presently preferred embodiments of the invention, which, together with the following examples, serve to explain the principles of the invention.

This invention provides a method for growing or propagating fastidious human viruses in the laboratory, a method of producing purified suspensions of these viruses, and such purified suspensions. The invention also provides methods for detecting the presence of a fastidious human virus in a sample, determining the infectivity of a sample which contains a fastidious human virus, and testing a substance to determine its activity against a fastidious human virus. As used herein, the term "fastidious human virus" means a human virus that replicates poorly or not at all in cell cultures or laboratory animals or is easily destroyed in the act of handling or processing in the laboratory. The terms "purified suspension", "purified virus suspension", or "purified viral suspension" means a collection of virus particles (virions) in a liquid which is free or essentially free of other viruses, cells, or microorganisms and in which a substantial number of the virions are capable of causing an infection in a human host.

The method of the present invention may be used to propagate any fastidious human virus. These include, but are not limited to, HPV, VZV, cytomegalovirus, and gastroenteritis viruses. The latter viruses include rotaviruses, Norwalk virus, Norwalk-like viruses, enteric adenoviruses, calciviruses, astroviruses, and coronaviruses. In a preferred embodiment, the method of the present invention is a method for growing HPV. It is particularly effective as a method for growing human papillomavirus type 11 (HPV-11), which causes vulvar warts and which, in turn, can cause vocal warts in newborns.

The first step in the method of the present invention involves the extraction of virus particles from human tissue, body fluids, or waste containing that virus. For example, VZV may be extracted from vesicular fluid obtained from the skin lesions of infected human hosts, and gastroenteritis viruses may be obtained from the feces of infected persons.

HPV may be extracted from infected human epithelial tissue. Such tissue may be identified by the epithelial or fibroepithelial projections or lesions known as papillomas. Such lesions are often removed in the course of medical treatment, such as the removal of warts. Another source may be tissue removed during autopsy. Since most papillomas contain little or no infectious virus particles, the tissue chosen should have detectable amounts of virus to produce an extract with a sufficient titer (number or concentration of infectious virions). For HPV-11, human genital epithelial tissue (including the cervix) is preferred, and vulvar condylomata acuminata is particularly preferred.

The virus may be extracted by known methods. For HPV, the preferred method is the one described in Kreider et al., *Nature*, 317: 639-641 (1985), incorporated herein by reference. Basically, this involves mincing the tissue containing the virus and then disrupting it in a tissue homogenizer. This step is necessary in order to free the virus from the keratinized tissue. Once the tissue has been homogenized, the solid material may be separated by known techniques, such as centrifugation. The supernatant will contain the virus.

The source of the virions and the techniques used to produce the extract must be chosen so that a sufficient titer is produced. Because of the lack of well-developed analytical techniques for fastidious human viruses, it is not possible to quantify what that titer should be. However, those skilled in the art will be able to take the appropriate measures to produce an extract with sufficient titer to allow the infection of the tissue to be placed beneath the renal capsule of the immuno-compromised animal. Generally, if the original source of the virus particles contains sufficient number of particles to be detected by known analytical techniques, an extract of sufficient titer can be prepared. If the original source contains significant or high amounts of virus particles, then the method of the present invention will result in the eventual production of an infected mass of tissue which, when removed from beneath the renal capsule, will have a moderate or high titer of virus particles.

The extract is used to infect human tissue that is susceptible to the virus in the extract. This is accomplished by using known techniques to incubate the extract with the tissue for a sufficient period of time to permit infection.

For HPV, the human tissue is epithelial tissue. The incubation period is generally approximately one hour, but the time is not critical. For HPV-11, the preferred epithelial tissue is human cervical tissue or human foreskin. Human neonatal foreskin is particularly preferred because of its abundance and ease of transformation. It is desirable but not necessary for the epithelial tissue to be relatively free of viruses, which is another reason that human neonatal foreskin is preferred. When human cervical tissue is used, it is desirable but not necessary that such tissue be taken from the squamo-columnar junction. It is expected that such tissue will be more likely to be able to be infected by the HPV because that site is where human cervical cancer generally arises.

The human tissue to be infected by the virus may be obtained as a result of surgical procedures or autopsies, and it may be prepared by any of several conventional techniques. It is preferred that the tissue be in the form of split-thickness grafts. The grafts should be prepared in a relatively aseptic environment in order to increase their chance of survival when transplanted to the immuno-comprised animal. The grafts may be held in Minimum Essential Medium to which an antibiotic has been added to prevent subsequent bacterial infection and to control any endogenous infection.

After incubation, the infected tissue is surgically placed beneath the renal capsule of an immuno-compromised animal. This may be done by the method disclosed in Kreider et al., *Nature*, 317: 639-641 (1985), incorporated herein by reference. Conventional measures are used to protect the immuno-compromised animal from infection and to permit a normal recovery. Immunocompromised rodents are preferred, and athymic (nude) mice are particularly preferred.

The grafts are placed beneath the renal capsule because such a placement has been found by the inventors to permit survival of a sufficient number of the grafts and production of sufficient quantities of infectious virions to permit the recovery and production of purified, high titer viral suspensions. For HPV, the inventors discovered that placing the grafts beneath the renal capsule permitted the successful morphologic transformation of the grafts and production of high titer viral suspensions, whereas placements in other areas of immuno-compromised animals, such as on the dorsal surface, have been unsuccessful so far.

The grafted tissue is permitted to remain for a period sufficient for the virus to multiply and a recoverable quantity of virions to be produced. The grafted tissue itself may grow, become transformed, or otherwise change.

In the case of HPV, the tissue becomes transformed by the virus. The virus grows in the tissue in sufficient quantities for recovery in approximately 3 to 5 months after the transplantation. Not every graft will persist, but approximately one-half will, forming cysts beneath the renal capsule. The cysts will take on the morphological features of papillomas. For example, when human condylomata acuminata are used as the source of the HPV, the cysts will take on the appearance of condylomata acuminata.

After 3-5 months, the virus may be recovered from the tissue beneath the renal capsule. Recovery may be made by sacrificing the animal and removing the tissue, from which the virus may be extracted by known techniques. Alternatively, the virus may be recovered while the tissue remains in the living animal through known techniques, such as surgical removal of part or all of the tissue.

The virus itself may be recovered from the tissue and purified by techniques known in the art. See Breedis et al., *Virology*, 17: 84-97 (1962), which is incorporated herein by reference. One such method is to homogenize the tissue, separate the homogenate by high and low speed centrifugation, and use cesium chloride density gradients to cause sedimentation of the virus particles. Under these conditions, the HPV will localize as a homogeneous band or bands at those densities which correspond to its bouyant density. This is at approximately 1.34 g/cc and slightly above. The purified HPV may then be diluted and stored using known techniques.

Purification of the recovered virus produces a purified suspension of the virions. Thus, the inventive method can be used to produce purified suspensions of fastidious human viruses such as HPV, VZV, cytomegalovirus, and the gastroenteritis viruses. Preferably, the purified suspension comprises HPV and most preferably it comprises HPV-11 or HPV-16. Purified HPV-11 produced by the method of the present invention has been found to be still infectious at a 1:100 dilution.

The purified suspensions of the present invention are useful reagents for research into the structure and function of fastidious human viruses. Purified HPV-16, for example, can be used to study its possible link with human cervical cancer.

In addition, the purified viruses of the present invention can be used for diagnostic purposes, for example, for the detection of antibodies to the virus. Such antibodies in fluids, tissues, or waste taken from a patient would indicate current or past exposure to the virus. The purified virus can also be used in tests of antiviral agents.

Purified virus may further be used for the production of specific antibodies, whether polyclonal or monoclonal, through known techniques. Such antibodies may be used for diagnostic and treatment purposes.

The purified virus may also be used to produce vaccines through known techniques involving attenuated or killed virus. The preparation of such vaccines and other useful compositions containing the purified virions produced by the present invention will be accomplished by those skilled in the art, given the teachings contained herein. Vaccines will comprise an effective amount of attenuated or killed virus in a pharmacologically acceptable carrier. Other appropriate adjuvants and auxilliary compounds may be added. The vaccines can be employed in any appropriate dosage forms, such as liquid solutions, suspensions, or elixirs. An inert, immunologically acceptable carrier is preferably used, such as saline or phosphate buffered saline. The preferred mode of administration of the vaccine is by parenteral administration.

Variations of the method of the present invention can also be used to detect the presence of a fastidious human virus in a sample taken from a patient, determine the infectivity of a sample containing such a virus, or test a substance to determine its antiviral activity. To detect the presence of the fastidious virus in a sample taken from a patient, the sample is incubated with tissue known to be susceptible to the virus. The tissue is then placed beneath the renal capsule of an immuno-compromised animal as explained previously. After a sufficient period of time has passed to allow the propagation of the virus if particles were present in the sample, the tissue is evaluated for the lesions or other effects caused by the virus. For HPV, for example, the tissue can be examined to see if it has been transformed into a cyst morphologically identical to a papilloma normally caused by that virus.

The ability of a sample containing a fastidious human virus to infect human tissue can also be assayed. This involves the preparation of serial dilutions of a viral suspension and the innoculation or application of the dilutions to tissue which is susceptible to the virus. This method does not actually measure the number of infectious particles in a suspension, but rather determines the extent to which a virus suspension can be diluted and still contain infectious virions. The end point of the method is usually the dilution that will infect 50% of the tissue samples brought into contact with the particular dilution. This value is an infectious dose$_{50}$ or ID$_{50}$.

In the context of the present invention, this method comprises preparing serial dilutions of the sample or viral suspension. For example, the dilutions could be 1:10, 1:100, 1:1000, etc. Each of the serial dilutions is then incubated with several pieces of human tissue known to be susceptible to the virus. Each of these pieces is then placed beneath the renal capsule of an immuno-compromised animal as previously described. The tissue is allowed to remain for a period of time sufficient to produce a lesion or other effect in the tissue the same or substantially identical to the lesion or effect produced by the virus when the virus naturally infects the human host. Each piece of tissue is then evaluated to determine if the lesion or effect has been produced. Determining which of the serial dilutions produced the effect in one half of the tissue samples that had been incubated with that dilution leads to $ID_{50}$ for the sample, which provides a measurement of its infectivity.

A substance can be evaluated for its antiviral activity against a fastidious human virus by determining its ability to prevent or otherwise lessen the effect of such a virus on susceptible human tissue which has been infected and placed in the immuno-compromised animal in the previously described way. The substance may be brought into contact with the infected tissue before the tissue is placed in the animal or it may be brought into contact with the susceptible tissue before the tissue is exposed to the virus and prior to being placed in the animal. For example, the substance can be placed on the surface of the tissue or injected or otherwise mixed into it. Alternatively, the substance may be administered systemically to the animal after the infected tissue has been placed beneath the renal capsule. Such administration may be parenterally or any other means which would be chosen by persons skilled in the art in view of the nature of the virus and the expected mode of action of the purported antiviral substance. Such substance could be a chemical, biological agent, or mixture of a number of such materials.

It is to be understood that the application of the teachings of the present invention to a specific problem or environment will be within the capabilities of one having ordinary skill in the art in light of the teachings contained herein. Examples of the products of the present invention and the processes for their production appear in the following examples.

EXAMPLES

Materials and Methods

Animals

Athymic mice (nu/nu on a BALB/c background) were purchased from Harlan Sprague Dawley, Inc., Madison, Wis. They were housed in flexible film isolators supplied with sterile air, water, and autoclaved laboratory chow supplemented with vitamins.

Preparation of Human Skin Grafts

Skin was obtained from 6 patients from various sites. Skin from all sites was subjected to both gross and microscopic examination and was free of detectable lesions. Split-thickness skin grafts were cut with a sterile double-edged razor blade clamped in a curved Kelly hemostat. Grafts were held in Minimum Essential Medium with only gentamycin (800 micrograms per milliliter) as supplement, and they were trimmed to dimensions of 2×2×0.5 mm. Grafts were then rinsed and incubated for 1 hour at 37° C. in 1 ml of one of two treatments: PBS (phosphate-buffered saline), or condylomata acuminata extract (C.A.).

Preparation of Condylomata Acuminata Extract

Vulvar condylomata were obtained from 15 female patients and stored at −70° C. until used. A total of 20 g was thawed, minced with scissors, and disrupted in 50 ml of PBS at 4° C. with a Virtis homogenizer at 25,000 rpm for 30 minutes. Cell-free supernatants and pellets were obtained by sedimentation at 1,000 g, separated, and stored at −70° C. The supernatant was used without further dilution to infect the skin grafts.

Grafting Technique

Each mouse was anesthetized with Nembutal, and the kidneys were delivered, one at a time, through dorsal, bilateral, paravertebral, subcostal incisions. The renal capsule was nicked, and a skin graft was placed in each kidney with toothless forceps. The skin incisions were closed with wound clips and the mice were given drinking water with trimethoprim (0.01 mg/ml) and sulfamethoxazole (0.05 mg/ml) for the duration of the experiment.

Histological Assessment of Grafts

Mice were killed by cervical dislocation and the kidneys were fixed in neutral-buffered formalin, embedded in paraffin, sectioned at 6 microns and stained with hematoxylin and eosin. Cohort sections were deparaffinized and incubated with antibody raised against disrupted bovine papillomavirus (Dakopatts, Accurate Chemical & Scientific Corp., Westbury, N.Y.) for the demonstration by the immunoperoxidase technique of the group-specific antigen (GSA). See Jensen, et al., *J. Natl. Cancer Inst.*, 64: 495–500 (1980) and Kurman, et al., *Am. J. Surg. Path.*, 7: 39–52 (1983), both of which are incorporated herein by reference. GSA is an internal capsid antigen common to most papillomaviruses. Positive controls consisted of canine papillomas or human vulvar condylomata. Negative controls were normal human skin.

Identification of HPV Genomes in C.A. and Transformed Grafts

Cloned DNAs of HPV 6, 11, 16, and 18 were graciously provided by Drs. Peter Howley (National Cancer Institute, NIH, Bethesda, Md.) and Harald zur Hausen (Freiburg, Federal Republic of Germany). Recombinant DNA constructs were transfected into *E. coli* (strain HB101) according to the method of Mandel and Higa, *J. Mol. Biol.* 53: 159–162 (1970), which is incorporated herein by reference. *E. coli* were grown in bulk, and plasmids were amplified with chloramphenicol. DNA was extracted with lysozyme and Triton X-100 and purified on cesium chloride/ethidium bromide equilibrium gradients. Plasmid identities were verified by cleavage with appropriate restriction endonucleases and agarose gel electrophoresis. Purified plasmids containing HPV DNAs were $^{32}P$ nick-translated to a specific activity of about $1 \times 10^8$ cpm per microgram DNA with the use of a commercial kit (Amersham, Arlington Heights, Ill.). HPV content of our infecting material was examined by Southern blot analysis. Phenol and phenol/chloroform extraction was used to extract high molecular weight DNA from the tissue pellet of the homogenized condylomata pool. DNA samples were precipitated with ethanol, resolubilized, bound to nitrocellulose filters and hybridized under stringent conditions (35.6% formamide, 10% dextran sulfate, 0.845M Na+, 46° C.) with the $^{32}P$ nick-translated HPV DNA probes. The filters were washed, dried, and exposed to X-ray film at −70° C.

EXAMPLE 1

Identification of HPV Genomes in Condylomata Extract

Previous analyses of the DNA contained in the infecting extract revealed hybridization to probes of HPV 11 DNA and, to a lesser extent, to HPV-6 DNA. To determine whether one or both viruses were present, Southern blot analysis was conducted on the DNA solubilized from the pellet of the C.A. used for infection of grafts in these and in past experiments. The results indicated that the DNA from the condylomata pool was not cleaved by EcoRl but was cleaved by Thal in a manner similar to the cleavage of the HPV-11 positive control. The results suggested that HPV-11 but not HPV-6 DNA was detected in the condylomata pool used as the infecting agent in these experiments.

EXAMPLE 2

Transformation of Adult Foreskin with Papillomavirus

The foreskin of a 29-year-old male was excised for phimosis. Split-thickness skin grafts were cut and exposed to PBS or C.A. The grafts were transplanted beneath the renal capsule of athymic mice and harvested between 96-128 days of growth (Table 1). Infection with the C.A. produced a two-fold enlargement in average graft diameters and caused morphological transformation in three of five grafts, but five of five were positive for GSA. Cells which were positive were abundant and exclusively found in the maturing, koilocytotic and parakeratotic layers. Both of the samples from four paired transformed grafts that were tested hybridized with the HPV-11 and HPV-6 probes and they did not react with the HPV-16 and 18 probes. This pattern of dot blot reactivity was identical to that seen in the infecting inoculum. Grafts which were infected with C.A. again demonstrated a two-fold enlargement in average graft diameter and 5 of 9 grafts were morphologically transformed. Eight of nine grafts were positive for GSA but none of two tested reacted with the HPV probes. Insufficient DNA sample recovery may explain the negative result in these two samples. Treatment with PBS alone induced no changes in the specified endpoints.

TABLE 1

Morphological transformation, group specific antigen expression, and HPV DNA content of human skin grafts infected with HPV from condylomata acuminata and transplanted beneath the renal capsule of athymic mice: foreskin, 29-year-old male.

| | Graft Treatment[a] | |
|---|---|---|
| | PBS | C.A. |
| Survival Frequency[b] | 2/6 | 5/5 |
| Days Harvested (range) | | (all groups) |
| Graft Diameters[d] | 4.0 ± 2 | 7.6 ± 1 |
| Transformed Grafts[d] | 0/2 | 3/5 |
| GSA+ Grafts[d] | 0/2 | 5/5 |
| HPV-11 Genome Detected[d] | 0/1 | 2/2 |

[a]C.A., condylomata acuminata extract
[b]Number of grafts which survived/total which were grafted
[c]mean ± SEM (mm)
[d]Number of samples which were positive/total which were tested. two grafts from each mouse were pooled for each sample. GSA+, group specific antigen positive

EXAMPLE 3

Transformation of Child Foreskins with Papillomavirus

Two siblings of 8 and 23 months of age received elective circumcisions. Split-thickness skin grafts were cut from the speciments. The grafts were exposed to C.A. or PBS and grafted beneath the renal capsule of athymic mice. After 98-130 days of growth, the grafts were examined. All of the 12 grafts from the 8-months-old male survived, whether they were from the control or the C.A.-treated groups (Table 2). The C.A.-infected grafts were about two-fold larger in average diameter than the controls. Four of six of the infected grafts were both morphologically transformed and GSA positive. Microscopically, the PBS-treated grafts were keratin-filled cysts lined by a slightly hyperplastic epithelium. The C.A.-infected cysts were extremely hyperplastic and the epithelium often contained papillary fronds with overlying parakeratosis. Cells of the maturing layers contained clear, perinuclear spaces with pynknotic, wrinkled nuclei characteristic of koilocytosis. Immunoperoxidase strain for the GSA demonstrated strong, positive staining of the nuclei in the maturing and keratinized layers; cells of the proliferating, basal layers were negative. The three C.A.-infected samples hybridized with both HPV-11 and HPV-6, but did not react with HPV-16 and HPV-18 (Table 2). The control grafts were negative for all endpoints studied.

TABLE 2

Morphological transformation, group specific antigen expression, and HPV DNA content of human skin grafts infected with HPV from condylomata acuminata and transplanted beneath the renal capsule of athymic mice: foreskin, 8-month-old male.

| | Graft Treatment | |
|---|---|---|
| | PBS | Condylomata Extract |
| Survival Frequency[a] | 6/6 | 5/5 |
| Days Harvested (range) | 98-130 | 98-130 |
| Graft Diameters[b] | 4.3 ± 0.7 | 8.3 ± 1.4 |
| Transformed Grafts[c] | 0/6 | 4/6 |
| GSA+ Grafts[c] | 0/6 | 4/6 |
| HPV-11 Genome Detected[c] | 0/3 | 3/3 |

[a]Number of grafts which survived/total which were grafted
[b]mean ± SEM (mm)
[c]Number of samples which were positive/total which were tested. two grafts from each mouse were pooled for each sample. GSA+, group specific antigen positive All of the grafts from the 23-months-old sibling also survived for 98-130 days when they were harvested (Table 3). The C.A.-infected grafts were 3-fold larger in average diameter than the controls. Nine of 11 of the C.A.-infected grafts were morphologically transformed, and 9 of 10 examined were GSA positive. The HPV-11 and HPV-6 probes hybridized ("dot blot") with all 4 of the C.A.-infected samples, but those samples did not hybridize with HPV-16 and HPV-18. The PBS-treated grafts morphologically resembled normal foreskin and were negative for all endpoints studied (Table 3). Three foreskin grafts from this patient were also subjected to Southern blot analysis after cleavage with restriction endonucleases. The results demonstrated that the transformed graft DNA was not cleaved by EcoRl but was cleaved by Thal in a manner similar to the cleavage of the HPV-11 positive control. Thus, only HPV-11 was detectable in the original, infecting C.A., and only HPV-11 was found in the grafts which were transformed with this material.

TABLE 3

Morphological transformation, group specific antigen expression, and HPV DNA content of human skin grafts infected with HPV from condylomata acuminata and transplanted beneath the renal capsule of athymic mice: foreskin, 23-month-old male.

| | Graft Treatment | |
|---|---|---|
| | PBS | Condylomata Extract |
| Survival Frequency[a] | 12/12 | 11/11 |

TABLE 3-continued

Morphological transformation, group specific antigen expression, and HPV DNA content of human skin grafts infected with HPV from condylomata acuminata and transplanted beneath the renal capsule of athymic mice: foreskin, 23-month-old male.

| | Graft Treatment | |
|---|---|---|
| | PBS | Condylomata Extract |
| Days Harvested (range) | 98-130 | 98-130 |
| Graft Diameters[b] | 3.0 ± 0.3 | 10.6 ± 1.1 |
| Transformed Grafts[c] | 0/11 | 9/11 |
| GSA+ Grafts[c] | 0/7 | 9/10 |
| HPV-11 Genome Detected[c] | 0/3 | 4/4 |

[a]Number of grafts which survived/total which were grafted
[b]mean ± SEM (mm)
[c]Number of samples which were positive/total which were tested. two grafts from each mouse were pooled for each sample. GSA+, group specific antigen positive

EXAMPLE 4

Transformation of Vulvar Skin with Papillomavirus

Split-thickness skin grafts were cut from a vulvectomy speciment freshly excised for squamous cell carcinoma in an 81-year old female. Only uninvolved skin was selected for experimental studies. Grafts were either exposed to PBS or infected with C.A. After 96-128 days of growth beneath the renal capsule, the grafts were removed and examined (Table 4). There were no differences in the average size of the C.A.-infected or control grafts. Four of the 13 C.A.-infected grafts were both morphologically transformed and GSA positive. 1 of 1 of the C.A.-infected samples was positive when hybridized with the HPV-11 and HPV-6 probes but none reacted with HPV-16 or HPV-18. All endpoints were negative in the PBS-treated control grafts.

TABLE 4

Morphological transformation, group specific antigen expression, and HPV DNA content of human skin grafts infected with HPV from condylomata acuminata and transplanted beneath the renal capsule of athymic mice: vulva, 81-year-old female.

| | Graft Treatment | |
|---|---|---|
| | PBS | Condylomata Extract |
| Survival Frequency[a] | 10/10 | 12/13 |
| Days Harvested (range) | 96-128 | 96-128 |
| Graft Diameters[b] | 3.9 ± 0.3 | 4.2 ± 0.3 |
| Transformed Grafts[c] | 0/10 | 4/13 |
| GSA+ Grafts[c] | 0/4 | 4/13 |
| HPV-11 Genome Detected[c] | 0/1 | 1/1 |

[a]Number of grafts which survived/total which were grafted
[b]mean ± SEM (mm)
[c]Number of samples which were positive/total which were tested. two grafts from each mouse were pooled for each sample. GSA+, group specific antigen positive

EXAMPLE 5

Transformation of Abdominal Skin with Papillomavirus

Abdominal skin from an 80-year old female who died of myocardial infarct was obtained from the midline epigastrium during autopsy. Split-thickness skin grafts were prepared and infected with the C.A. as described. Infected and control grafts were harvested after 42-158 days of growth beneath the renal capsule of athymic mice (Table 5). Most of the grafts survived the growth period and formed keratin-filled epidermal cysts. There were no differences in survival frequency or size of the grafts in C.A.-infected or control grafts. None of the histological changes which are associated with condylomatous transformation were found in any of the grafts. Two of the 9 infected grafts were positive for GSA, despite the lack of morphological transformation. DNA from a total of 8 control grafts (paired from the right and left kidneys of a single nude mouse) and 6 C.A.-infected grafts (similarly paired) was analyzed by the "dot blot" analyses for sequences hybridizing with the HPV probes. All 3 of the paired samples from the 6 C.A.-infected grafts hybridized with probes of HPV-11 DNA, and to a lesser extent with HPV-6, but they did not react with HPV-16 or HPV-18 probes. All of the control samples failed to react with any of the HPV probes.

TABLE 5

Morphological transformation, group specific antigen expression, and HPV DNA content of human skin grafts infected with HPV from condylomata acuminata and transplanted beneath the renal capsule of athymic mice: abdominal skin, 80-year-old female.

| | Graft Treatment | |
|---|---|---|
| | PBS | Condylomata Extract |
| Survival Frequency[a] | 9/10 | 9/12 |
| Days Harvested (range) | 88-158 | 42-158 |
| Graft Diameters[b] | 5.6 ± 0.8 | 4.8 ± 0.5 |
| Transformed Grafts[c] | 0/9 | 0/9 |
| GSA+ Grafts[c] | 0/9 | 2/9 |
| HPV-11 Genome Detected[c] | 0/4 | 3/3 |

[a]Number of grafts which survived/total which were grafted
[b]mean ± SEM (mm)
[c]Number of samples which were positive/total which were tested. two grafts from each mouse were pooled for each sample. GSA+, group specific antigen positive

EXAMPLE 6

Transformation of Lower Leg Skin with Papillomavirus

Split-thickness skin grafts were cut from the pre-tibial region of a lower limb which had been freshly amputated from an 80-year old male with peripheral vascular disease. The skin grafts were exposed to either the C.A. or PBS and grafted beneath the renal capsule. The grafts were harvested after 91-150 days of growth. The results demonstrated that there were no significant differences in the frequency of graft survival or the size of the grafts at harvest. Two of 20 grafts infected with C.A. were morphologically transformed by the usual histological criteria (Table 6). Those same 2 grafts were also positive for the GSA. None of the control grafts were morphologically transformed or GSA positive. Dot blot analysis revealed that 3 of the 5 samples were positive for both HPV-11 and HPV-6, but they did not hybridize with the HPV-16 or HPV-18 probes. No control samples reacted with any of the probes.

TABLE 6

Morphological transformation, group specific antigen expression, and HPV DNA content of human skin grafts infected with HPV from condylomata acuminata and transplanted beneath the renal capsule of athymic mice: lower leg skin, 80-year-old male.

| | Graft Treatment | |
|---|---|---|
| | PBS | Condylomata Extract |
| Survival Frequency[a] | 13/22 | 20/24 |
| Days Harvested (range) | 91-150 | 91-150 |
| Graft Diameters[b] | 4.7 ± 0.7 | 4.8 ± 0.4 |
| Transformed Grafts[c] | 0/13 | 2/20 |
| GSA+ Grafts[c] | 0/12 | 2/19 |
| HPV-11 Genome Detected[c] | 0/4 | 3/5 |

[a]Number of grafts which survived/total which were grafted.
[b]mean ± SEM (mm)
[c]Number of samples which were positive/total which were tested. two grafts from each mouse were pooled for each sample. GSA+, group specific antigen positive

EXAMPLE 7

Morphological Transformation of Human Vocal Cord by HPV-11

The purpose of these experiments was to determine if human vocal cord grafts, place beneath the renal capsule, could be transformed with HPV-11. True vocal cords were obtained at autopsy from three patients who were deceased less than 10 hours. These included a 53 year old male, a 4 month old female, and a 5 year old female. Split-thickness grafts were cut from the appositional surfaces of both cords. They were then treated with either PBS or HPV-11 and grafted beneath the renal capsule of the athymic mice. They were removed after 3-4 months of growth. The cysts which had formed were usually filled with clear mucous. An accumulation of squames was present in 3 of the 21 HPV-11 infected grafts. Only one of the infected grafts was substantially larger than the controls. Microscopic sections of the 18 PBS-treated grafts revealed that they were lined by pseudostratified, ciliated, columnar epithelium. The cells often contained mucous-filled vacuoles. In contrast, 9 of the 21 HPV-11 infected grafts showed focal, nodular proliferations of squamous epithelium, sometimes at multiple loci within a single cyst. The squamous cells in these foci were sometimes koilocytotic with clear spaces surrounding the nuclei. Multiple nuclei were often found within single cells, but the nuclei were not hyperchromatic or wrinkled as they were in comparable infected grafts of cervix or skin. We have defined this appearance as a "squamous metaplasia", and we believe that it is a transitional morphology, preliminary to the formation of the squamous laryngeal papillomas. In 3 of the 21 HPV-11 infected grafts, true squamous papillomas were found. Sections of these lesions were stained for the group specific antigen, but only equivocal reactions were observed. There was insufficient material for dot blot analysis of the HPV genomes present. The observations were essentially similar for all patients studied, with no correlation with age.

These data suggest that HPV-11 can morphologically transform human vocal cord epithelium. This tissue is more resistant to infection than cervix or skin. The rate of growth of the transformed cells is slower. This tissue did not produce HPV-11.

EXAMPLE 8

Production of Purified HVP-11

Athymic mice (nu/nu on a Swiss background) were purchased from Mammalian Genetics, National Cancer Institute, Bethesda, Md. The mice were placed in flexible film isolators supplied with sterile air, food and water. Foreskins were obtained from neonatal circumcisions and were free of gross or microscopic lesions. Split-thickness skin grafts were cut with a sterile single-edged razor blade or a scalpel. Grafts were held in Minimum Essential Medium with only gentamycin (800 micrograms per milliliter) supplement, and they were trimmed to dimensions of $2 \times 2 \times 0.5$ mm. Grafts were then rinsed and incubated for 1 hr at 37° C. in 0.1 ml of one of two treatments: PBS (phosphate-buffered saline), or a PBS extract of natural vulva condylomata acuminata (designated CA 1). The extract contained HPV-11 by Southern blot analysis and was free of detectable HPV-1, 6, 16, and 18. The mice were anesthetized, and the kidneys were exposed through dorsal incisions. The renal capsule was nicked and a skin graft inserted with a toothless forceps. Skin incisions were closed with wound clips.

After 3-5 months of growth, the mice were killed by cervical dislocation. Foreskin grafts transformed by HPV-11 often produced think-walled condylomatous cysts 1-2 cm in diameter. They were incised and the keratin cores removed for virus extraction. Conventional paraffin sections were prepared from the condylomatous cyst walls and stained with H&E and with the immunoperoxidase method for the demonstration of the group-specific antigen (GSA) of the papillomaviruses. Jenson, et al., *J. Natl. Cancer Inst.*, 64: 495-500 (1980), incorporated herein by reference. These sections showed typical condylomatous changes, consisting of koilocytosis, hyperplasia, and hyperkeratosis. GSA-positive nuclei were often abundant. For electron microscopy, grossly papillomatous regions of the interior cyst wall were identified with a dissecting microscope and 1 mm cubes were excised, fixed and sectioned. Many of the koilocytotic nuclei contained intranuclear arrays of virions that were internal to the heterochromatic nuclear margin. The intranuclear location of abundant virions strongly argues against the possibility that this is input virus. The original inoculum ought to be randomly distributed and is most unlikely to persist in the koilocytotic layers of an epithelial population which has renewed itself many-fold over a period of several months.

The preceding Examples demonstrated by Southern blot hybridization that experimental condylomata contained HPV-11 and were negative for HPV-1, 6, 16, and 18. In this Example, experimental and natural condylomata were directly compared for the relative amounts of hybridizable HPV-11 DNA and biological infectivity for a new generation of human foreskin grafts. For this purpose, approximately 7.8 g of four, experimentally-produced condylomata (about 1.5 cm diameter each) were pooled, homogenized and extracted with PBS and clarified by low speed centrifugation. This extract of experimental condylomata was designated CA 2. HPV-11 DNA content of naturally-occurring (CA 1) and experimentally-induced condylomata (CA 2) were compared. The direct comparison of the amount of HPV-11 in CA 1 with CA 2 is valid since the ratio of condylomata mass to solvent was the same in both cases. The reactivity of the natural condylomata DNA (CA 1) was extinct at a dilution of 1:16, whereas the experimental condylomata DNA (CA 2) was first negative at a dilution of 1:64. Thus, both the experimentally-induced and the natural condylomata contained similar amounts of HPV-11 DNA.

The CA 2 extract of experimental condylomata also was used to infect fresh foreskin grafts. Three independent experiments were conducted to determine the infectivity of laboratory-produced HPV-11. In the first, a total of 32 CA 2 infected grafts were placed beneath the renal capsule of athymic mice. After 3 months of growth, the mice were killed and the grafts examined. Ten grafts did not "take", but of the 22 remaining, 16 (73%) were condylomatous. The second experiment demonstrated that 36 of 38 (95%) foreskin grafts were transformed by CA 2, forming condylomatous cysts averaging 1 cm in diameter at 4 months after infection. These proportions of transformed grafts were similar to that which we found after infection with the CA 1 extract of naturally-occurring vulvar condylomata. In the third experiment, serial dilutions to the base 10 of extracts of both the natural (CA 1) and experimental (CA 2) condylomata were compared.

The results demonstrated that both preparations were highly infectious when undiluted or diluted to $10^{-1}$ or $10^{-2}$. Higher dilutions were negative. The recovery of virus from the grafts 3—4 months after infection that was infectious at a dilution of $10^{-2}$ is strong evidence for HPV replication in the infected grafts.

A small aliquot of the CA 2 extract was centrifuged in a CsCl gradient. Blot hybridization was used to identify the position of HPV-11 DNA. The results indicated that all of the HPV-11 DNA was present at a gradient density of 1.34 g/cc. This corresponds to the expected density for HPV virions and not to the density of free DNA.

HPV-11 was purified in bulk from experimental grafts by the following preparative method. A second extract (CA 3) of the experimental condylomata was first produced and the virus was extracted by homogenization, differential centrifugation, and high and low speed centrifugation, followed by sedimentation in cesium chloride density gradients. Examination of the CsCl gradient with a perpendicular light beam demonstrated an opalescent band about 1 mm thick, located at a density of 1.34 g/cc. Fractions of 0.25 ml were collected by bottom puncture of the gradient and 50 microliters of each fraction were spotted on cellulose nitrate paper. The fractions were subjected to alkali to denature the protein and render the DNA single-stranded as described by Grunstein and Hogness, *Proc. Natl. Acad. Sci. U.S.A.*, 72: 3961-3965 (1975), incorporated herein by reference. The samples were hybridized with $^{32}P$ nick-translated HPV-11 probe. The results were identical to the data for CA 2, except that the amount of virus DNA was much greater. This reflects the difference in the original inoculum. Fraction 5 was then dialyzed overnight against NT buffer, and a drop examined by electron microscopy. Virions were abundant in the preparation, and their appearance was consistent with that of an HPV.

It will be apparent to those skilled in the art that various modifications and variations can be made to the processes and products of the present invention. Thus, it is intended that the present invention cover the modifications and variations of this invention, provided they come within the scope of the appended claims and their equivalents.

We claim:

1. A method to detect the presence of a fastidious human virus selected from the group consisting of human papillomavirus, varicella-zoster virus, cytomegalovirus, and gastroenteritis virus in a sample comprising the steps of:
   incubating said sample with human tissue known to be susceptible to said fastidious human virus;
   placing said human tissue beneath the renal capsule of an immuno-compromised animal;
   allowing said tissue to remain in said immuno-compromised animal for a period of time sufficient to produce an effect in said tissue that is caused by said virus when said virus infects said tissue; and
   determining if said effect has been produced in said tissue.

2. A method to determine the infectivity of a sample of a fastidious human virus selected from the group consisting of human papillomavirus, varicella-zoster virus, cytomegalovirus, and gastroenteritis virus comprising the steps of:
   preparing serial dilutions of said sample;
   incubating each of said serial dilutions with pieces of human tissue known to be susceptible to said virus;
   placing each of said pieces of human tissue beneath the renal capsule of an immuno-compromised animal;
   allowing each of said pieces of human tissue to remain in said immuno-compromised animal for a period of time sufficient to produce an effect in said tissue that is caused by said virus when said virus infects said tissue;
   determining if said effect has been produced in each of said pieces; and
   determining the infectivity of said sample by determining which of said serial dilutions produced said effect in one half of the pieces of human tissue incubated with said dilution.

3. A method for testing a chemical or biological substance to determine its antiviral activity against a fastidious human virus selected from the group consisting of human papillomavirus, varicella-zoster virus, cytomegalovirus, and gastroenteritis virus comprising the steps of:
   infecting human tissue known to be susceptible to said fastidious human virus with said virus;
   placing said infected tissue beneath the renal capsule of an immuno-compromised animal;
   administering said substance to said animal;
   allowing said tissue to remain in said animal for a period of time sufficient to produce an effect in said tissue that is caused by said virus when said virus infects said tissue; and
   determining if said effect has been produced.

4. The method of claims 1, 2, or 3 wherein said fastidious human virus is varicella-zoster virus, cytomegalovirus, or a gastroenteritis virus.

5. The method of claims 1, 2, or 3 wherein said fastidious human virus is a human papillomavirus (HPV).

6. The method of claim 5 wherein said HPV is HPV-11.

7. The method of claim 5 wherein said HPV is HPV-16.

8. The method of claim 5 wherein said susceptible tissue is epthelial tissue.

9. The method of claim 6 wherein said susceptible tissue is genital tissue.

10. The method of claim 9 wherein said genital tissue is cervical tissue.

11. The method of claim 10 wherein said cervical tissue was taken from the squamo-columnar junction.

12. The method of claim 9 wherein said genital tissue is foreskin.

13. The method of claim 12 wherein said foreskin is neonatal foreskin.

14. The method of claims 1, 2, or 3 wherein said animal is a rodent.

15. The method of claim 14 wherein said rodent is an athymic mouse.

16. The method of claim 5 wherein said period of time is approximately three to five months.

17. The method of claim 5 wherein said HPV is HPV-11 or HPV-16, said susceptible tissue is epithelial tissue, said animal is a rodent.

18. The method of claim 17 wherein said period of time is approximately three to five months.

19. The method of claim 18 wherein said epithelial tissue is genital epithelial tissue and said rodent is an athymic mouse.